United States Patent
Smith

(10) Patent No.: US 7,977,326 B2
(45) Date of Patent: Jul. 12, 2011

(54) SUPPORTIVE TREATMENT OF LIVER DISEASE

(76) Inventor: Howard J Smith, Templestowe (AU)

( * ) Notice: Subject to any disclaimer, the term of this patent is extended or adjusted under 35 U.S.C. 154(b) by 458 days.

(21) Appl. No.: 11/547,469

(22) PCT Filed: Apr. 21, 2005

(86) PCT No.: PCT/AU2005/000561
§ 371 (c)(1),
(2), (4) Date: Aug. 6, 2007

(87) PCT Pub. No.: WO2005/102353
PCT Pub. Date: Nov. 3, 2005

(65) Prior Publication Data
US 2007/0292507 A1 Dec. 20, 2007

(30) Foreign Application Priority Data

Apr. 22, 2004 (AU) ............ 2004902151
May 7, 2004 (AU) ............ 2004902447

(51) Int. Cl.
*A61K 31/00* (2006.01)
*A61K 31/425* (2006.01)

(52) U.S. Cl. .... 514/183; 514/894; 514/365; 514/211.06

(58) Field of Classification Search ............ 514/211.06, 514/365, 894
See application file for complete search history.

(56) References Cited

U.S. PATENT DOCUMENTS 5,854,233 A * 12/1998 McLean .......... 514/211.07
6,214,385 B1 * 4/2001 Heinicke et al. ....... 424/497
2003/0049840 A1  3/2003 Demetriou

OTHER PUBLICATIONS

Hisanaga, M et al. J. Surg. Res. 55: 404-410, 1993.*
Satorres, J et al. Liver 15: 16-19, 1995.*
Lukienko, P.I. et al. Bulletin of Exptl. Biol. and Med. 130: 874-876, 2000.*
Rajaraman et al. J. Pharm. Pharmaceut Sci 10(3):380-387, 2007.*
Mayo clinic , "Toxic Hepatitis: Introuduction," http://www.mayoclinic.com/health/toxic-hepatitis/DS00811.*
Mayo clinic Toxic Hepatitis Prevention http://www.mayoclinic.com/health/toxic-hepatitis/DS00811.*
Mayo clinic Toxic Hepatitis Treatment http://www.mayoclinic.com/health/toxic-hepatitis/DS00811.*
National Heart Lung and Blood Institute- CCBs review http://www.dhhs.gov/news/press/1995pres/950831d.html.*
Farghali et al. (Physiol. Res. (2000); 49:261-268).*
Lukienko et al. (Bulletin of Experimental Biology and Medicine (2000); 9:874-876).*
Kappus et al. (Experientia (Dec. 1981); 37(12):1233-1241).*
Levy et al (Digestive Diseases and Sciences (Mar. 2002); 47(3):543-548).*

* cited by examiner

*Primary Examiner* — Frederick Krass
*Assistant Examiner* — Chris E Simmons
(74) *Attorney, Agent, or Firm* — Bio Intellectual Property Services LLC; O. (Sam) Zaghmout

(57) ABSTRACT

The invention provides a composition and method for treatment of a subject suffering from liver disease comprising the oral administration of a slow release formulation of calcium channel blocker such as diltiazem and thiamine which is also an antioxidant which is relatively hydrophilic when compared with the calcium channel blocker.

4 Claims, No Drawings

SUPPORTIVE TREATMENT OF LIVER DISEASE

FIELD

The present invention relates to a method of supportive treatment of liver disease and its complications including cirrhosis of the liver and portal hypertension. In particular, the invention applies to non-malignant liver disease including viral or toxic hepatitis where direct or indirect damage to the liver cell membranes, which is secondary to the primary disease process, initiates a cascade of cell swelling, hypoxia, and impaired liver function over and above that caused by the primary disease process.

BACKGROUND

Liver diseases include toxic hepatitis such as alcoholic hepatitis and cirrhosis, hepatitis C, which is the most common viral hepatitis, and less commonly the immunological liver diseases characterised by chronic inflammation.

Therapeutic attempts to improve liver function have always been secondary to treatment of the primary disease processes, but there have been many attempts to improve function by targeting different components of the pathological processes. One key method employed has been the use of antioxidants beginning with the herbal extracts silymarin and silibinin (reviewed by Flora et al, 1998). However, the efficacy of silymarin has been disappointing in alcoholic liver disease (Angulo et al, 2000), and there is the potential for hepatotoxic effects (Bass; 1999). More recently, tocopherol, dipyridamole (Novikov et al, 1991; Vargas et al, 2001), and a range of modern, both synthetic and naturally-occurring, antioxidants have been used (Vaidya et al. 1996)

Included among these are the calcium blocking agents verapamil, diltiazem, and amlodipine (Mason et al, 1999), and also nitrendipine (Thurman and colleagues, 1998). At first, it was thought that these agents acted directly on liver cells to block calcium entry as they do in excitable tissues such as the myocardium and in arteries (Liang and Thurman, 1992), however, it was soon realised that the liver does not have voltage-gated calcium channels, which are the target of these drugs in excitable tissues. Therefore, if these drugs were acting on the liver, they needed to act in a different way. Thus, it was found that many calcium blockers were also powerful antioxidants (Heo et al, 1997).

It has also been proposed that calcium channel blockers may dilate the hepatic artery to increase delivery of oxygenated blood to the liver (McLean. 1998). However, the protective effect of drugs such as verapamil, diltiazem (Liang and Thurman, 1992; Romero and colleagues, 1994) and the other calcium blockers occurs in isolated cells. The effects on hepatic arterial blood flow of calcium blockers administered orally in low doses have not been confirmed. Diltiazem has also been shown to have no effect on microvascular blood flow within the liver (Marteau and colleagues, 1988).

Patents suffering hepatitis have an impaired ability to absorb thiamine and yet thiamine concentration in the blood is often difficult to measure. The production of energy in the mitochondria is thus severely compromised in cells of a diseased liver.

The discussion of the background to the invention herein is included to explain the context of the invention. This is not to be taken as an admission that any of the material referred to was published, known or part of the common general knowledge as at the priority date of any of the claims.

SUMMARY

We have found that the interaction of the effects of a calcium channel blocker (particularly diltiazem) that exerts its calcium blocking effect on mitochondria, has antioxidant effects and is relatively lipophilic, and the B-vitamin thiamine, which is a relatively hydrophilic antioxidant when compared with the calcium channel blocker, provides a significant improvement in liver disease. While thiamine is frequently ineffectual in diseased cells, we believe the co administration of a calcium channel blocker with these properties facilitates action of thiamine, protects cell membranes, and enables continued production of energy when cells are damaged.

In accordance with the present invention, we provide a method of treatment of a subject suffering from liver disease comprising the administration of (i) an oral slow release formulation of a relatively lipophilic calcium channel blocker with antioxidant effects and (ii) the B vitamin thiamine, which is also an antioxidant and which is relatively hydrophilic when compared with the calcium channel blocker.

The invention also provides the use of (i) a relatively lipophilic calcium channel blocker with antioxidant effects and (ii) the B vitamin thiamine, which is also an antioxidant and which is relatively hydrophilic when compared with the calcium channel blocker in preparation of a medicament for treatment of liver disease by co administration thereof in one or more compositions for providing slow release of calcium channel blocker.

The invention further provides a pharmaceutical composition for treatment or prevention of liver disease comprising (i) a relatively lipophilic calcium channel blocker with antioxidant effects and (ii) the B vitamin thiamine, which is also an antioxidant and which is relatively hydrophilic when compared with the calcium channel blocker. The pharmaceutical composition is typically a slow release composition.

The liver-selective slow release formulation is required because many of the drugs suitable for this treatment are vasoactive or have systemic effects that may be avoided if they are concentrated preferentially within the liver. The low dose slow release composition will preferably provide a delivery rate of calcium channel blocker sufficient to provide a clinical effective blood level in the portal vein and less than required to provide a clinically effective level in the peripheral circulation to thereby provide a delivery rate having a selective effect in the liver.

The thiamine may be administered separately or concurrently but it is preferred that it is administered in the same composition with the calcium channel blocker.

Thiamine, which is well known as a B vitamin acting within mitochondria as a mitochondrial protective agent, that is, as a cofactor of pyruvate dehydrogenase, is also a hydrophilic antioxidant. It is used in patients with nutritional deficiency and in some patients with viral hepatitis. The addition of thiamine to the calcium antagonist with antioxidant properties also exploits both the facilitator effect of the vitamin on energy production within mitochondria, and its own antioxidant effect within the cell.

DETAILED DESCRIPTION

The method of the invention involves the administration of a relatively lipophilic calcium channel blocker with antioxidant effects and thiamine, which is a relatively hydrophilic antioxidant when compared with the calcium channel blocker.

Preferably the calcium channel blocker is administered at a daily dose which is less than half (more preferably less than one third) of the dose prescribed for treatment of cardiovascular disease. The dose prescribed for treatment of cardiovascular disease is provided in medical texts relating to prescription drugs. We have referred, in particular, to doses of calcium channel blockers including diltiazem approved for use in Australia (Australian Edition of MIMS Annual 2002). The approved optimum dose for diltiazem is 180 to 240 mg per day.

The preferred calcium channel blockers are lipophilic to ensure that they penetrate deep with cells and within membranes so that their therapeutic effect is located where free radicals are acting. By contrast, drugs acting within the cytosol or cellular milieu need to be more hydrophilic. Most calcium blocking drugs including verapamil, diltiazem, amlodipine, and nitrendipine have a membrane stabilizing effect but the shorter half-life of diltiazem and verapamil makes these agents more suitable for formulation as a liver-selective membrane-stabilizing agent. The preferred agent is diltiazem administered as a slow release formulation at doses of less than 70 mg per day and preferably less than 50 mg per day. These doses are much lower that the doses of the drug used in the treatment of angina and hypertension. Diltiazem may be in the form of the hydrochloride salt or other pharmaceutically acceptable salt.

The preferred calcium channel blocker will be a membrane-stabilizing agent (or combination of agents) which has effects across several of the principal components of the membrane destructive process. The preferred calcium channel blocker will act as an intracellular and intramembranous antioxidant, limit calcium entry into the mitochondria, and inhibit phospholipase activity, and to facilitate or maintain energy production by the cells. Furthermore, these actions preferably continue to operate as the cell pH falls during hypoxia. Together we believe these effects act to reduce cell swelling and hypoxia, and thence to improve liver function. We have found diltiazem to be particularly preferred on these bases.

Diltiazem, which is cis-(+)-3-(acetyloxy)-5-[2-(dimethylamino)ethyl]-2,3-dihydro-2-(4-methoxyphenyl)-1,5-benzothiazepin-4(5H)-one, referred to herein as "diltiazem", is a benzothiazine derivative possessing calcium antagonist activity. Diltiazem has heretofore been used clinically to block the influx of calcium ions in smooth and cardiac muscle and thus exert potent cardiovascular effect. Diltiazem has been shown to be useful in alleviating symptoms of chronic heart disease, particularly angina pectoris and myocardial ischemia and hypertension, while displaying a low incidence of side effects. In these uses diltiazem is available as diltiazem hydrochloride in tablet form in strengths of 30, 60, 90 and 120 mg. and in capsule form in strengths of 60, 90, 120, 180, 240 and 300 mg. Diltiazem is also available in injectable form with a strength of 5 mg./ml.

Diltiazem therapy for treatment of cardiovascular disease typically starts with 30 mg. administered 4 times daily. The dosage is gradually increased to 180 to 240 mg./day and sometimes up to 360 mg./day, given in divided doses three or four times daily, at one- to two-day intervals until an optimum response is obtained. The liver extensively metabolizes Diltiazem. According to professional use information issued by Marion Merrell Dow Inc., diltiazem in CARDIZEM® brand tablets is absorbed to about 80% and is subject to an extensive first-pass effect, giving an absolute bioavailability, compared to intravenous administration, of about 40%. Single oral doses of 30 to 120 mg. of CARDIZEM® diltiazem tablets result in peak plasma levels two to three hours after administration. Detectable plasma levels occur within 30 to 60 minutes after administration indicating that CARDIZEM® diltiazem tablets are readily absorbed. The plasma elimination half-life following single or multiple administration is approximately 3.5 hours. Therapeutic blood levels of CARDIZEM® diltiazem tablets appear to be in the range of 50 to 200 ng./ml.

In contrast with prior art formulation of calcium channel blockers the first pass clearance of drugs such as diltiazem, which is viewed as an impediment to effective treatment of cardiovascular disease, becomes a virtue in treating liver disease as it allows the clinical effect of the drug to be confined to the liver. Accordingly it is particularly preferred that the calcium channel blocker be present in a low dose and as a slow release formulation to provide a clinical effective blood level in the portal vein and a dose less than required to provide a clinically effective level in the peripheral circulation. The method and composition of the invention thus provide a delivery rate having a selective effect on the liver.

This method of hepatic protection using diltiazem in combination with thiamine, applies to any disease state of the liver in which the cell membranes have been damaged either primarily or secondarily by oxidising agents or oxidising processes. The use of a liver-selective formulation of these lipophilic membrane-stabilizing agents is complementary to the treatment of the primary disease.

When appropriate these liver-protective agents may be co-prescribed or co-formulated with therapeutic agents used in the primary management of the disease, such as ribavirin or other orally-administered antiviral agent in the management of hepatitis C.

The invention thus also provides a method of treatment or prevention of liver disease by administering at least one active agent selected from portal hypertensive agents and antiviral agents wherein said at least one active agent is co-administered with a liver-selective formulation of a lipophilic membrane stabilizing agent and antioxidant such as diltiazem, with hydrophilic antioxidant agent such as thiamine.

The two components of membrane stabilization, that is, calcium channel blocker plus the hydrophilic antioxidant thiamine may be co-formulated or may be administered in a separate composition. The agents may be administered by the same route (particularly oral administration) or may be administered by different routes. For example, one active agent may be administered intravenously or parenterally and the calcium channel blocker (membrane stabilizing) agent or agents administered orally.

In the method and composition of the invention thiamine may be used as the salt from such a hydrochloride salt or other pharmaceutically acceptable derivative.

In one particularly preferred embodiment of the invention at least one agent selected from portal hypertensive agents and antiviral agents is co-formulated with calcium channel blocker and thiamine.

The most preferred antiviral is ribavirin which may (and preferably will) be used in combination with interferon. Accordingly in a further embodiment the invention provides a method for treatment of viral hepatitis comprising co-administering a liver-selective formulation of a membrane stabilizing agent with ribavirin and preferably also interferon.

Ribavirin and the membrane stabilizing agent are preferably administered orally and more preferably co-formulated to provide controlled release of each agent. Interferon is preferably administered parenterally to provide an effective level during co-administration.

In a further embodiment the invention provides a method of treatment or prevention of toxic hepatitis (for example alcoholic hepatitis) comprising co-administering the liver selective formulation of a lipophilic calcium channel blocker and thiamine. It is particularly advantageous if thiamine, which is hydrophilic, is co-formulated with the calcium channel blocker component. Accordingly in the preferred embodiment we provide a composition for treatment of toxic hepatitis comprising a liver selective formulation of a calcium channel blocker such as diltiazem with the relatively hydrophilic agent thiamine.

The preferred calcium channel blocker is diltiazem in an amount of from 20 to 70 mg/day and more preferably 25 to 50 mg/day.

When thiamine is used it is preferably present in an amount to provide delivery of from 1 to 5 mg per day and more preferably 1 to 3 mg per day. In individual cases, including acute treatment, and at the discretion of the attending physician, higher doses up to 20 mg per day may be used.

When ribavirin is used in the treatment viral hepatitis, doses of up to 1200 mg per day are used in conventional formulations, or in doses of less than 500 mg/day, as a liver-selective formulation.

Throughout the description and claims of the specification the word "comprise" and variations of the word, such as "comprising" and "comprises", is not intended to exclude other additives, components, integers or steps.

In accordance with the present invention, we provide a method of pharmaceutical therapy comprising the administration of a liver-selective formulation of a calcium channel blocker, which is a relatively lipophilic antioxidant, in an amount sufficient to provide an inhibitory effect on mitochondrial calcium channels, and an inhibition of phospholipase. The lipophilic agent may be prescribed with or without addition of a hydrophilic antioxidant so that there is an additive antioxidant effect within the cell cytosol or milieu as well as within the cell membranes. The use of the vitamin thiamine adds a complementary mitochondrial effect in the mitochondria where as a co-factor of pyruvate dehydrogenase, that facilitates energy production. This therapy may be used to protect the liver and maintain hepatic function when the liver has been damaged by any form of chronic non-malignant disease in which the cell membranes have been damaged either by primary or secondary processes such that the liver cells swell sufficient to impede portal venous blood flow and cause hypoxia of the liver.

We have found that the combination of calcium channel blocker and thiamine provide a membrane-stabilizing effect. The term "membrane-stabilizing" was coined many years ago to define local anaesthetic and other membrane effects of beta-adrenergic antagonists. The term now embraces a range of membrane effects, which in turn need to be characterised individually (Smith, 1982).

Diseases in which the treatment of the present invention may have application include all forms of viral hepatitis (including hepatitis C), alcoholic liver disease, cirrhosis of the liver, toxic hepatitis, autoimmune hepatitis, damage to the liver sustained during chemotherapy or radiotherapy, and ageing of the liver.

Pathology of Chronic Liver Disease

Progressive deterioration of the structure and function of cell membranes within the liver is a key component of almost all forms of chronic, non-malignant liver disease. It contributes to the overall impairment of liver function, leads to cell death, and complements or enhances the effects of the primary disease processes.

Membrane deterioration, or destabilisation, is caused by at least six inter-related processes, of which a common feature is the generation of free radicals (superoxide anion, hydroxy radicals, and others) and their oxidising effects on phospholipids in cell membranes to produce lysophospholipids.

First, the primary disease process may generate free radicals. In the case of viral hepatitis, including Hepatitis C, the free radicals are not produced by the virus, but by the immune systems within the body that have been activated in response to the viral infection (Patrick, 1999; Jain et al, 2002; Loguercio and, Federico, 2003.)

The immune systems act in the tissues where the virus is growing to oxidise phospholipid particularly in the external membranes of the liver cells to cause structural and functional changes that increase the permeability of the membranes to water, sodium ions and calcium ions. This process induces cell swelling and calcium overload as the intracellular calcium ion concentration rises above physiological levels. Similar processes in alcoholic liver disease, toxic hepatitis, autoimmune hepatitis, chemotherapy and the ageing liver also act to oxidise the cell membranes, induce cell swelling and produce calcium overload.

Second, the cell swelling caused by the change in membrane permeability increases resistance to blood flow through the liver and through the portal venous system. The liver is particularly prone to reduction in blood flow when cell swelling occurs, because in contrast to other organs, most of its blood supply is at low pressure through the portal venous system, and with the low oxygen content characteristic of venous blood. Even modest inhibition of blood flow causes hypoxia within the liver sufficient to impair hepatic function over and above that caused by the primary disease processes.

Third, progressive hypoxia causes both the intracellular and intramitochondrial levels of $NADPH_2$ to rise. This in turn stimulates production of free radicals that in contrast to those produced by immune or toxic effects on the outside of the cells, is within the cells and the mitochondria. Thus, the immune or toxic responses cause membrane damage from outside in, but the immediate effect of hypoxia is to cause membrane damage from inside out.

Fourth, the rising levels of calcium ions activate ion-gated calcium channels within the mitochondrial membranes (black lipid) so that calcium is concentrated preferentially within mitochondria. This causes the mitochondria to divert their function away from energy production and give priority to calcium extrusion. As a result, the rising mitochondrial concentration of calcium during hypoxia acts to increase the functional effects of hypoxia and to increase $NADPH_2$ levels further.

Fifth, the rising intramitochondrial levels of calcium act to accelerate the production of free radicals by $NADPH_2$. Thus, the rate of progressive membrane deterioration or destabilisation increases as mitochondrial calcium accumulation progresses.

Sixth, the rising intramitochondrial levels of calcium activate phospholipase, which in turn brings a second destructive process to cell membranes throughout the liver cells.

These six processes interact with each other to create progressive membrane oxidation and dysfunction, cell swelling, hypoxia, calcium accumulation, phospholipase activation, impairment of hepatic function and eventual cell death.

To be effective in liver cells that have been damaged by hypoxia or other processes that oxidises phospholipid in cell membranes, a hepatoprotective membrane-stabilizing effect needs to fulfil the following criteria:

- The agent should act as an antioxidant to absorb or destroy free radicals that are induced by high levels of $NADPH_2$, which occur in hypoxia and other forms of oxidative damage.
- The agent should exert its membrane protective and antioxidant effect both within cells and within membranes where the free radicals are being formed and where they are doing damage.
- The agent should act as an antioxidant within mitochondria.
- The agent should inhibit mitochondrial calcium channels to reduce the elevation of $NADPH_2$ that occurs during hypoxia.
- The agent should permit the mitochondria to continue to produce ATP under conditions of calcium overload of the cells.
- The agent should prevent activation of phospholipase by increasing concentrations of calcium.
- The agent should prevent or reduce reduction in blood supply caused cell swelling and the oxidative changes in cell membranes.

All of these qualities are shown by several calcium blocking drugs including D-diltiazem, however, the protective effects of any such agent are independent of the known vasodilator effects that calcium blocking agents have on the systemic circulation and are independent of change in the supply of oxygenated arterial blood.

There are specific calcium carrying channels in mitochondrial membranes (black lipid) that respond to calcium channel blocking drugs (Spalletti-Cernia et al, 2002). While these channels are ion-gated rather than voltage-gated, they have features in common with the channels in excitable tissues and this appears to explain their response to drugs such as verapamil, diltiazem, and amlodipine. The immediate effect of mitochondrial calcium channel blockade is to limit entry of calcium into the mitochondria when the channels are activated by rising intracellular calcium concentrations, and thereby protect the mitochondrial function. Limitation of calcium entry reduces the activation of phospholipase (Draper et al, 2004) although this may also be a direct effect of the drugs on this enzyme system.

To be effective as a membrane hepatoprotectant, a membrane-stabilizing agent needs to be relatively lipophilic. The target of the free radicals produced by primary disease processes or by hypoxia is the phospholipid within the cell membranes. It follows that antioxidant activity must operate within the lipid bio-layer, that is, within the cell membranes where the free radicals are exerting damage. Similarly, membrane protective agents must protect black lipid (mitochondrial membranes) to inhibit the ion-gated calcium channels present within these membranes. However, we propose that a simultaneous effect within the cell cytosol provided by a hydrophilic antioxidant adds to the total antioxidant protection. While the key actions required are to prevent the destructive effects of free radicals within the cell membranes including the mitochondrial membranes, it is also helpful to neutralise the free radicals within the cytosol or hydrophilic fraction.

Lipophilicity also contributes to the desirable profile of agents suitable for presentation as a liver-selective formulation. This requires that a drug has a short half-life on account of hepatic metabolism, and that the drug is reliably absorbed across the gastro-intestinal wall after release from a capsule or other formulation descending through the gastrointestinal tract. Lipophilic agents cross cell membranes readily thereby fulfilling these criteria. Any antioxidant or other stabilising agent selected and active for its hydrophilic nature needs to mildly lipophilic to meet these criteria of half-life and gastrointestinal absorption. Thiamine meets these criteria.

A second approach to improve hepatic function has been to administer the B-vitamin thiamine. Thiamine acts as a co-factor on the mitochondrial enzyme pyruvate dehydrogenase to facilitate energy production by the mitochondria. While it is well known that patients with alcoholic liver disease may be deficient in this enzyme, it has also been shown that patients with viral hepatitis may benefit from its administration (Wallace and Weeks, 2001). Recent studies have also described the antioxidant properties of thiamine (Lukienko et al, 2000). In contrast to diltiazem, thiamine is a relatively hydrophilic molecule.

Presentation of a lipophilic and hydrophilic membrane-stabilizing drug as a liver-selective formulation is a key part of this invention.

The concept of liver-selective drug delivery requires that a drug with a short half-life be administered as low dose and as a slow-release or controlled-release formulation so that the drug is released slowly over several hours—preferably up to 24 hours. After crossing the gastrointestinal wall, the drug reaches the relatively small volume of the portal venous system and is carried to the liver. Here a significant portion is removed from the circulation by metabolism with the remainder passing into the much larger volume systemic circulation. In this way, a stable concentration gradient is achieved where the concentration of the drug is up to 5 or more times higher in the liver and portal circulation than in the systemic circulation. The achieved concentration gradient may be higher in cirrhosis or other conditions with sluggish portal circulation, however, this effect may be offset by the development of significant collateral vessels between the portal and systemic circulations.

In many therapeutic situations it is desirable to limit delivery of a drug to the target organ. This is particularly important when a drug has side effects related to other pharmacological properties. In the case of membrane-stabilizing agents that are also calcium channel blockers (and potent vasodilators), their presentation as liver-selective therapy avoids or minimises the risk of unwanted vasodilator and cardiac effects thereby increasing tolerance and acceptability. Liver-selective delivery also reduces the total daily dose of a drug required to 20-25% of the full systemic dose that would normally be required if the drug was being administered to achieve a systemic effect.

In the case of diltiazem, where the doses required for systemic effects used in the treatment of angina pectoris and hypertension are generally in the range of 120-360 mg/day, a dose of 50 mg or less per day of diltiazem will retain a therapeutic effect in the liver but not the rest of the body.

A membrane-stabilizing agent with these properties and including diltiazem formulated for liver-selective delivery with or without thiamine can be used to protect the liver in:

Viral hepatitis including Hepatitis B, and C, and other forms.
Alcoholic hepatitis
Cirrhosis of the liver
Portal hypertension
Other forms of non-malignant liver disease caused by toxins, drugs, and abnormal immune states.
Liver dysfunction during chemotherapy.
Liver dysfunction after radiotherapy
The ageing liver.

In the case of viral hepatitis, the immediate cause of damage to liver cell membranes is the body's immune response to the presence of the virus. (Loguercio and Federico, 2003). This leads to generation of free radicals with damage to cell membranes on the surface and the inside of the cell (Jain et al, 2002). It follows that while the use of interferon with or without added ribavirin (or related molecules) is necessary antiviral treatment, there is a need to protect or reverse damage done to the liver cell by the immune processes. Therefore a liver-selective membrane-stabilizing agent with both antioxidant and mitochondrial effects is complementary to the primary treatment. Furthermore, in those communities of people who cannot afford expensive virucidal therapy, treatment with a liver-selective membrane-stabilizing agent such as diltiazem or related molecules that can minimise or contain symptoms becomes an affordable alternative. A liver-selective membrane-stabilizing agent with or without added thiamine can therefore be prescribed as monotherapy, be co-prescribed with interferon and ribavirin or with other appropriate antiviral therapy, or be co-formulated with ribavirin or other orally-administered component of the antiviral therapy so that both or all drugs are administered together as a liver-selective formulation.

Treatment with thiamine (Vitamin B1) has been used in management of alcoholic liver disease because patients with this disease frequently have a nutritional deficiency of the vitamin. Thiamine acts as a co-enzyme for several reactions that cleave carbon-carbon bonds including key metabolic processes within the hepatic mitochondria (Wilson, 1998). In addition to correction of nutritional deficiency, treatment with thiamine may improve drug-induced mitochondrial damage in patients with hepatitis B and C (Kontorinis and Dieterich, 2003). Other workers have shown that thiamine deficiency is common in patients with cirrhosis caused by both alcoholic liver disease and Hepatitis C, but not in Hepatitis C without cirrhosis (Levy and colleagues, 2002). However, thiamine has been shown to improve liver function in patients with Hepatitis B (Wallace and Weeks, 2001). These workers have suggested that the vitamin may have a protective effect on mitochondrial function in patients with viral hepatitis. Another key component of the protective affect of thiamine it its antioxidant properties, which appear to be active in the cytosol on account of its hydrophilic profile.

Evidence is accruing that treatment with thiamine (vitamin) may be helpful in patients with viral hepatitis as a mitochondrial protective agent (Wallace A E and Weeks W B, 2001), and particularly in those patients with cirrhosis caused by hepatitis C (Levy et al, 2002). Co-prescription or co-formulation of a liver-selective membrane-stabilizing agent and thiamine may be helpful in these patients. In particular we believe the complementary energy-facilitating role of thiamine and its antioxidant effect together with the membrane stabilizing agent provide a significant advantage.

In alcoholic hepatitis at least three pathological actions are operating. First, the alcohol itself sets up oxidising reactions in which the membranes are damaged by free radicals. The resultant cell swelling caused by entry of water and ions through the now permeable membranes creates cell swelling and relative hypoxia. In addition, people with chronic alcoholic liver disease are frequently nutritionally deficient so that thiamine deficiency impairs the mitochondrial efficiency. While the best treatment for these patients is withdrawal of alcohol together with appropriate nutrition including administration of thiamine, the use of a liver-selective membrane-stabilizing agent with both antioxidant and mitochondrial calcium inhibition is complementary to the primary treatment. The agent may be prescribed as monotherapy, be co-prescribed with thiamine, or be co-formulated with thiamine, so that both agents are administered together as a liver-selective formulation.

In patients with portal hypertension and cirrhosis, the immediate treatment is correction of the underlying causative liver disease, and then reduction of the vascular resistance to portal venous flow, or immediate reduction of portal venous flow with propranolol or other non-selective beta-adrenergic antagonist. Therefore a liver-selective membrane-stabilizing agent with both antioxidant and mitochondrial calcium inhibition is complementary to this primary treatment. The agent may be prescribed as monotherapy, or co-prescribed with propranolol.

In other forms of liver disease including toxic hepatitis, immune hepatitis, and damage to the liver during the course of systemic chemotherapy, attack of the cell membranes of the liver cell by oxidising agents and free radicals from both within and without the cell is the principle pathological mechanism of the disease. This in turns causes the cells to swell inducing hypoxia with a second stage of free radical production throughout the cell and the mitochondria. Radiotherapy also generates free radicals. While this may be a key mechanism targeted at organs with cancer when the liver is irradiated either necessarily or intentionally, the normal physiology with low pressure perfusion by portal venous blood makes the organ particularly at risk of hypoxia and deterioration of function. Therefore a liver-selective membrane-stabilizing agent or agents with both antioxidant and mitochondrial calcium inhibition is complementary to drug or toxin withdrawal, management of the immune disease, treatment with systemic chemotherapy, or after radiotherapy.

In the ageing liver, there is a reduction of the oxidising properties of the liver such that the liver is less able to protect itself from naturally occurring oxidising effects in the diet. These changes, which involve both mitochondrial and cytoplasmic function, make the liver more at risk of cell swelling, modest hypoxia and impaired function. Therefore a liver-selective membrane-stabilizing agent or agents with both antioxidant and mitochondrial calcium inhibition is useful treatment for management of the ageing liver to help maintain hepatic function in older patients with any degree of impaired hepatic function.

This protective effect of a membrane-stabilizing agent with antioxidant effects, mitochondrial calcium inhibition, and antiphospholipase activity administered as monotherapy, co-prescribed with other agents, or co-formulated with other agents, prevents or reduces the oxidising effect of the free radicals on cell membranes, the subsequent production of lysophospholipid, and the overall destruction of cell membranes. In this way, the cell membranes of hepatocytes, which are vulnerable to free radicals during hypoxia, retain their relative impermeability to both sodium and water with the result that there is less cell swelling and less progression of hypoxia. In addition, the retention of permeability and the effect of mitochondrial calcium inhibition protect the cells from calcium overload and impaired mitochondrial function so that there is inhibition of free radical production within the mitochondria, and more preservation of the metabolic function of the liver cells than in untreated hypoxic hepatocytes.

Interaction of Diltiazem and Thiamine

We believe that the antioxidant effects of diltiazem and thiamine within the cell membranes (diltiazem) and cytosol (thiamine) are additive, and probably independent.

A different situation occurs within the mitochondria because the drug appears to have little or no effect in health but the effect of diltiazem becomes activated during calcium overload. By contrast, thiamine acts within normal mitochondria but appears to be inhibited or become ineffectual as intramitochondrial calcium concentrations rise. Therefore the protective effect of diltiazem on mitochondrial calcium content allows the effect of thiamine to continue to operate during disease conditions. Thus the effects of diltiazem and thiamine within the mitochondria are synergistic or enabling.

The combination of diltiazem and thiamine on diseased liver cells act in at least four ways. Their antioxidant effects on the whole cell are additive. Their intramitochondrial effects are synergistic or enabling. The paired cell and mitochondrial effects can be described as complementary.

Formulation for Slow-Release

There are many techniques to effect slow release of an active pharmaceutical agent from an orally-administered formulation. These methods may include techniques designed to delay the disintegration of a capsule, tablet, or other vehicle, techniques designed to delay the solubility of a capsule, tablet or other vehicle, and techniques in which an active agent may be bound to a polymer or other large molecule such that absorption can not take place until the substance has been released from the polymer or other large molecule. The means of achieving these different methods of slow release are varied and include well-known older methods, such as layers of shellac coating, and more modern techniques using synthetic and cellulose polymers or providing a membrane coating with at least one pore.

The dosage forms according to the present invention may be controlled-release dosage forms. The mechanism of release of these dosage forms can be controlled by diffusion and or erosion. In some embodiments, the formulation comprises polymer-coated multiparticulates, polymer-coated tablets or minitablets, or hydrophilic matrix tablets.

A slow-release formulation of a membrane-stabilizing drug designed to act as a hepatoprotective agent may be designed to release the drug over a period of about 6 to about 24 hours following administration, thereby permitting once-a-day administration and providing a sustained exposure of the drug to the liver. In some embodiments, formulations releasing the drug over extended periods of time may have more than one timed-release component to affect time coverage.

The present invention relates to the finding that a protective effect of low-doses of membrane-stabilizing agents (including diltiazem at doses of less than 50 mg/day) administered as a slow release formulation, is mediated by a direct protective effect on the liver itself rather than on the vasculature, that the drug acts as a lipophilic antioxidant to penetrate cells and protect both cell membranes and mitochondria from the damaging effects of phospholipid oxygenation, and that it acts as a mitochondrial calcium antagonist.

The slow release composition may be of a type previously reported for treatment of cardiovascular disease with the exception that the dose of Diltiazem is reduced to within the range of from 20 to 70 mg per day. As discussed above the slow release composition will preferably also contain thiamine in an amount of from 1 to 20 mg per day, preferably 1-5 mg per day. The composition may be designed for once daily administration, twice daily administration or more often but once daily administration is particularly preferred.

U.S. Pat. Nos. 4,721,619, 4,891,230, 4,917,899 and 5,219,621 disclose diltiazem formulations that purport to require administration once every twelve hours (i.e., twice a day). U.S. Pat. Nos. 4,894,240 and 5,002,776 disclose diltiazem formulations that purport to require administration once every 24 hours (i.e., once a day). To obtain the dissolution profiles disclosed in these patents, the formulations disclosed require a multi-layer membrane that coats the central core and an organic acid in the active core and/or in the multi-layer membrane. Suitable organic acids disclosed in these patents are adipic acid, ascorbic acid, citric acid, fumaric acid, malic acid, succinic acid and tartaric acid. According to professional use information issued by Marion Merrell Dow Inc., the CARDIZEM® CD diltiazem capsule is a sustained release diltiazem capsule containing 120, 180, 240 or 300 mg. diltiazem hydrochloride with a suggested dosage of one capsule a day. Similarly, to obtain a 24-hour diltiazem release profile, the pellets in the CARDIZEM® CD diltiazem capsule include fumaric acid, an organic acid, and a multi-layer membrane that coats the central core. According to the aforementioned patents, the pellets must be dried for a number of hours during and after the coating process.

Another approach which may be adapted for use in the process of the invention is described in U.S. Pat. No. 5,834,024 (Heinicke et al) which uses a combination short lag and long lag pellets of diltiazem to provide a uniform release of diltiazem over a 24 hour period.

In one embodiment of the composition of the invention the slow release composition comprises a core containing diltiazem and one or more polymeric coatings. The core may and preferably will contain the thiamine component. The core may be formed on a seed of, for example, an inert material such as a sugar sphere. Pharmaceutically acceptable binders such as hydroxypropyl cellulose may be used in the core. The one or more coatings may comprise a polymer which is permeable to diltiazem and water and a polymer which is relatively less permeable to diltiazem and water.

An example of a diltiazem permeable polymer is the cationic polymer synthesized from acrylic and methacrylic acid ester with a low content of quaternary ammonium groups, known as EUDRAGIT RL (manufactured by Rohm Pharma GmbH) ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly (ethylene terephthalate), poly(vinyl isobutyl ether), poly(vinyl acetate), poly(vinyl chloride) or polyurethane or a mixture of any two or more of these. Suitable naturally occurring polymers or resins that are less permeable to water and diltiazem include shellac, chitosan, gumjuniper or a mixture of two or more of these.

Substances that can be used that are less permeable to diltiazem and water include a cationic polymer known as EUDRAGIT RS (manufactured by Rohm Pharma GmbH. EUDRAGIT RS is less permeable than EUDRAGIT RL because EUDRAGIT RS has fewer ammonium groups) ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly (vinyl chloride) or polyurethane or a mixture of any two or more of these. Suitable naturally occurring polymers or resins that are less permeable to water and diltiazem include shellac, chitosan, gumjuniper or a mixture of two or more of these.

In addition to the polymers, the coating layer includes a lubricant and a wetting agent. Preferably the lubricant is talc and the wetting agent is sodium lauryl sulfate.

Suitable alternatives for sodium lauryl sulfate may include agents such as acacia, benzalkonium chloride, cetomacrogol emulsifying wax, cetostearyl alcohol, cetyl alcohol, cholesterol, diethanolamine, docusate sodium, sodium stearate, emulsifying wax, glyceryl monostearate, hydroxypropyl cellulose, lanolin alcohols, lecithin, mineral oil, monoethanolamine, poloxamer, polyoxyethylene alkyl ethers, polyoxyethylene castor oil derivatives, polyoxyethylene sorbitan fatty acid esters, polyoxyethylene stearates, propylene glycol alginate, sorbitan esters, stearyl alcohol and triethanolamine, or a mixture of any two or more of the foregoing.

Suitable alternatives for talc that may be included in the coating are calcium stearate, colloidal silicon dioxide, glycerin, magnesium stearate, mineral oil, polyethylene glycol, and zinc stearate, aluminium stearate or a mixture of any two or more of the foregoing.

A plasticizing agent is preferably included in the coating to improve the elasticity and the stability of the polymer film and to prevent changes in the polymer permeability over prolonged storage. Such changes could affect the drug release rate. Suitable conventional plasticizing agents include acetylated monoglycerides, acetyltributylcitrate, acetyltriethyl citrate, castor oil, citric acid esters, dibutyl phthalate, dibutylsebacate, diethyloxalate, diethyl malate, diethylfumarate, diethylphthalate, diethylsuccinate, diethylmalonate, diethyltartarate, dimethylphthalate, glycerin, glycerol, glyceryl triacetate, glyceryltributyrate, mineral oil and lanolin alcohols, petrolatum and lanolin alcohols, phthalic acid esters, polyethylene glycols, propylene glycol, rape oil, sesame oil, triacetin, tributyl citrate, triethyl citrate, and triethyl acetyl citrate, or a mixture of any two or more of the foregoing. Triethyl citrate is the presently preferred plasticizing agent.

Alternatively or in addition the core or coating may comprise an organic acid such as adipic acid, ascorbic acid, citric acid, fumaric acid, malic acid, succinic acid, tartaric acid and fumaric acid.

An alternative method of controlled release is to use membrane coating about a core comprising the active agents which membrane has at least one pore therein. Such an arrangement is described by Chen et al in U.S. Pat. No. 6,866,866 for providing slow release of metformin for a once a day dose. Chen et al also describe a slow release formulation for diltiazem in U.S. Pat. No. 6,524,620 which may be utilised with the low dose composition of the invention for treatment of liver disease.

The invention will now be described with reference to the following examples. It is to be understood that the examples are provided by way of illustration of the invention and that they are in no way limiting to the scope of the invention.

EXAMPLES

Example 1

In Vitro Studies

Hepatoprotective Effect of Diltiazem

The protective effect of diltiazem on cell membranes was examined in piglet hepatic microsomal membranes obtained from the livers of 3-week-old female piglets. The microsomal; fraction was treated with either vaso-active D-diltiazem, or the vaso-inactive L-diltiazem (0-1000 µM) for one hour at 37° C. followed by one hour of the free radical generator AAPH (2,2'-azobis-(2-amidinopropane) dihydrochloride). Following incubation the microsomal mixture was centrifuged at 2000 rpm to remove excess AAPH and diltiazem. The extent of reactive oxygen species mediated lipid peroxidation in the microsomal membranes was then measured employing the fluorescence market dichlorofluoresen (DCF, 10µ for 15 min). Image analysis. The results obtained from image analysis showed that D-diltiazem, but not L-diltiazem, produced a dose-dependent inhibition of membrane oxidation as shown by reduction in DCF activity in AAPH induced free radical release.

TABLE 1

DCF activity in AAPH induced free radical release in microsomes treated with D-diltiazem

|  | Control | 1000 | 500 | 250 | 50 | 5 |
| --- | --- | --- | --- | --- | --- | --- |
|  | Dose D-diltiazem (µM) | | | | | |
| Average | 56482 | 27258 | 31498 | 35148 | 38293 | 44501 |
| SEM | 1330 | 601 | 865 | 371 | 688 | 158 |
|  | Dose L-diltiazem (µM) | | | | | |
| Average | 54973 | 49937 | 53182 | 51120 | 49949 | 52799 |
| SEM | 1477 | 1429 | 2506 | 1108 | 874 | 894 |

These studies, commissioned by the inventor and undertaken by Prof F Burczynski of the University of Winnipeg, suggest that diltiazem has a hepatoprotective property that is independent of its vascular pharmacological properties. In parallel studies using H2O2 as a free radical generator, diltiazem was not protective. It was concluded that H2O2 acts in cytosol (hydrophilic phase) rather than at or near lipophilic membranes.

Example 2

Hepatoprotective Effect of Diltiazem Plus Thiamine

Hepatic liver microsomes were obtained from 4 healthy piglets as described previously. Microsomes were stored at −80° C. until required for study. Concentration of microsomes was 1 mg/ml. Diltiazem concentrations were 50 and 500 µM, Thiamine concentrations tested included 10, 50, and 100 µM. Free radical generator AAPH was 1 mM. The study detected hepatic lipid peroxidation products by analyzing the fluorescence activity of the dye DCFH by a plate reader as described in our previous report.

DCF-DA was treated with 2M NaOH and MeOH for 2 hours and after which time it was neutralized with HCl to yield the intracellular form of DCFH as described by the manufacturer. Hepatic microsomes were diluted to 1 mg/ml using Phosphate Buffered Saline (PBS). Microsomes were incubated with various concentrations of diltiazem, thiamine or in combination at 37° C. for 1 hour. Control microsomes were incubated with PBS (no drug treatment). Microsomal mixture was then incubated with 1 mM AAPH for 1 hour to initiate free radical induced lipid peroxidation for 1 hour at 37° C. Following incubation, the microsomal mixture was centrifuged at 2000 rpm using 5000 MWCO ultracentrifuge tubes and the procedure repeated twice with PBS to remove any AAPH and drug. Lipid peroxidized microsomes were incubated with 10 μM DCFH for 15 minutes and fluorescence activity recorded using a fluorescence plate reader.

Table 1 shows results from all studies (n=6). The addition of thiamine to microsomes substantiated reduced the fluorescence activity (i.e., suppressed free radical release). Overall the addition of diltiazem to thiamine resulted in a further reduction of fluorescence activity ($p<0.05$). The reduction in activity was significant at low and high doses of diltiazem. The addition of diltiazem produced a greater reduction in fluorescence activity, the reduction seemed to be additive.

TABLE 2

Suppressive effects of diltiazem and thiamine on fluorescent activity (free radical release).

| | Fluorescence Activity | | | | | |
|---|---|---|---|---|---|---|
| μM | Control | Thiamine (T) 10 | 50 | 100 | Diltiazem (D) 50 | 500 |
| Mean | 39260 | 31113 | 27265 | 23477 | 36492 | 32271 |
| SEM | 993 | 414 | 737 | 448 | 235 | 453 |

| | Diltiazem & Thiamine | | | | | |
|---|---|---|---|---|---|---|
| μM | D50& T10 | D50& T50 | D50& T100 | D500& T10 | D500& T50 | D500& T100 |
| Mean | 29219 | 26318 | 22014 | 28892 | 23468 | 21200 |
| SEM | 690 | 595 | 204 | 453 | 590 | 180 |

These studies suggest that diltiazem and thiamine have additive antioxidant and protective effects on the isolated liver cell acting on the cell cytosol, and microsomal membranes.

Example 3

Hepatoprotective Effect of Diltiazem Plus Thiamine in Mitochondria

Studies in mitochondrial suspensions may be undertaken to examine the effect of the combination of diltiazem and thiamine on energy production.

Suspensions of rat mitochondria are examined to determine their integrity by measuring the ability of ADP to stimulate oxygen production. As an additional control study the production of ATP in the mitochondria may also be examined.

Diseased cells may be simulated by increasing the calcium concentration in the perfusate. Examination of the effect of each of thiamine and diltiazem separately and their combination may be carried out to demonstrate that diltiazem facilitates the improved energy production in a diseased cell. Indeed the combined use is believed to provide synergy as thiamine is ineffectual in diseased cell mitochondria.

Example 4

Hepatoprotective Effect in Patients

The following clinical protocol may be used to study and validate the hepatoprotective effect of low-dose, slow-release diltiazem
Clinical Protocol Ten or more patients with hepatitis C who have not been treated with antiviral therapy or who have not responded to treatment with interferon with or without ribavirin, will be recruited into a study examining the effects of 25 mg and 50 mg of diltiazem in a slow-release formulation. Each patient should have stable but abnormal liver function tests as evidenced by elevated plasma concentrations of ALT (amino-alanine-transferase) Preference should be given to patients who do not have H.I.V. infection, or in whom there is a significant alcohol intake problem. Each formulation will be given as a once-daily dose for fourteen days.

The hepatoprotective effect of low dose, slow-release diltiazem on the liver will be measured objectively by assessing the change in ALT levels, and subjectively by assessing the symptomatic status of the patient with respect to fatigue and well-being. In a formal clinical trial, the latter will require double-blind—placebo-controlled studies with appropriate questionnaires to assess quality of life.

At the discretion of the clinical investigator, the study may permit patients to increase dosage from 25 mg per day to 50 mg per day at the end of a 14-day treatment. However, rather than expecting a greater effect with the higher doses, the differential efficacy between these doses is more likely to be a function of an individual's severity of disease where more severe restriction of portal venous flow creates a higher concentration of drug within the liver, and thence the opportunity to employ the lower doses.

It is expected that the 25 m and 50 mg liver-selective formulations of diltiazem will lower ALT levels towards normal, and that patients will note less lethargy and fatigue as their liver function improves.

Co-Prescription and Combination Therapy

Because the use of a liver-selective membrane-stabilizing agent with both antioxidant effect and mitochondrial calcium inhibition (such as diltiazem) is a complementary therapy, a liver selective formulation of such a drug will frequently be co-prescribed with antiviral treatment (such as ribavirin) in the treatment of viral hepatitis, thiamine in the case of alcoholic hepatitis, or propranolol in the case of portal hypertension.

Example 5

Controlled Release Formulation of Calcium Channel Blocker and Relatively Hydrophilic Antioxidant The following controlled release formulation may be prepared:
Core
Drug component: 2 to 70% w/w of a mixture of diltiazem (20 to 70 mg) thiamine (1 to 20 mg)
Binder: 3 to 98% by weight
Coating
Membrane Polymer: 50 to 99%
Flux enhancer: 0 to 40%
Plasticiser: 0 to 30%

Example 6

The following low dose slow release formulation for release over 12 hours may be prepared by the method of U.S. Pat. No. 5,834,024:
Core
Diltiazem: 30 mg
Thiamine: 3 mg
Hydroxypropyl cellulose 3.5 g
Sugar spheres 28 g
Coating
Eudragit RL: 0.5 g
Eudragit RS: 6.8 g
Triethyl citrate 0.7 g
Sodium lauryl sulfate 0.2 g
Talc 4.1 g

Example 7

The following slow release capsule formulation may be prepared by the method of U.S. Pat. No. 6,074,669

| Ingredients | mg/capsule |
|---|---|
| Diltiazem Hydrochloride | 40 |
| thiamine | 2 |
| Eudragit L-100 | 65 |
| Methocel K-100-M | 175 |
| Hydroxypropylcellulose (HPC-M) | 125 |
| Lactose | 100 |
| Magnesium Stearate | 7 |
| Aerosil | 8 |
| Total | 720 |

Example 8

The following method may be used to prepare controlled a release formulation of diltiazem and thiamine in accordance with the method of U.S. Pat. No. 5,616,345.

Diltiazem hydrochloride (250 g), thiamine hydrochloride (25 g) adipic acid (0.5 kg) and talc (0.100 kg) are blended and milled through a No. 50 mesh screen so as to obtain a homogenous powder.

The powder may be applied to starch/sugar seeds (0.6-0.71 mm diameter) (0.5 kg) in a standard coating pan using a coating solution of:

| | |
|---|---|
| 10% Polyvinylpyrrolidone | 80 parts by weight in isopropanol |
| 5% Ethylcellulose | 20 parts by weight in isopropanol |

The seeds are coated with a measured volume of coating solution followed by dusting on of a measured weight of the powder mix. The coated seeds are allowed to dry and the coating step repeated until all of the powder has been applied. The coated seeds defining active cores are then dried overnight to remove all traces of solvent.

The active cores of the pellets being prepared may then be surrounded by a membrane solution consisting of:

| | |
|---|---|
| 5% Ethylcellulose | 90 parts by weight in isopropanol |
| 5% Polyvinylpyrrolidone | 10 parts by weight in isopropanol |

Each coat of membrane solution may comprise 5 ml of solution per kg of coated seeds.

REFERENCES

Angulo P, Patel T, Jorgensen R A, Therneau T M, Lindor K D. Silymarin in the treatment of patients with primary biliary cirrhosis with a suboptimal response to ursodeoxycholic acid. *Hepatology* 32: 897-900, 2000 Comment in: Hepatology 33: 483-4, 2001

Bass N M. Is there any use for nontraditional or alternative therapies in patients with chronic liver disease? *Curr Gastroenterol Rep* 1: 50-6, 1999.

Draper D W, Harris V G, Culver C A, Laster S M. Calcium and its role in the nuclear translocation and activation of cytosolic phospholipase A (2) in cells rendered sensitive to TNF-induced apoptosis by cycloheximide. *J. Immunol.* 172:2416-23, 2004

Flora K, Hahn M, Rosen H, Benner K. Milk thistle (*Silybum marianum*) for the therapy of liver disease. *Am J Gastroenterol* 93: 139-43, 1998 Comment in: *Am J Gastroenterol* 94:545-6, 1999.

Jain S K, Pemberton P W, Smith A, McMahon R F, Burrows P C, Aboutwerat A, Warnes T W. Oxidative stress in chronic hepatitis C: not just a feature of late stage disease. *J Hepatol.* 36:805-11, 2002.

Kontorinis N and Dieterich D. Hepatoxicity of antiretroviral therapy. *AIDS Rev.* 5: 36-43, 2003.

Levy S, Herve C, Delacoux E and Erlinger s. Thiamine deficiency in hepatitis C virus and alcohol-related liver diseases. *Dig Dis Sci* 47: 543-8, 2002

Loguercio C, Federico A. Oxidative stress in viral and alcoholic hepatitis. *Free Radic Biol Med.* 34:1-10, 2003

Lukienko P I. Mel'nichenko N G, Zverinskii I V and Zabrodskaya S V Antioxidant properties of thiamine *Bull Exp Bio Med* 130: 874-6, 2000

McLean A J. Method of treating liver disease and like indications with vasodilating agents. U.S. Pat. No. 5,854,233 Dec. 29, 1998.

Novikov K N, Herrera M, Pascual C, Gonzalez R The antioxidative activity of drugs in the liver microsomal system of rats *Nauchnye Doki Vyss Shkoly Biol Nauki.* 12:19-27, 1991.

Patrick L. Hepatitis C: epidemiology and review of complementary/alternative medicine treatments. *Altern Med Rev* 4:220-38, 1999

Smith H J. The need to redefine membrane-stabilizing activity of beta-adrenergic receptor antagonists. *J Mol Cell Cardiol.* 14:495-500, 1982.

Spalletti-Cernia D, D'Agnano I, Sorrentino, R. Zupi, G, Vecchio G, Portella G and Laccetti P. Verapamil reverts resistance to drug-induced apoptosis in Ki-ras-transformed cells by altering the cell membrane and the mitochondrial transmembrane potentials. *Oncol Res.* 13:25-35, 2002

Thurman R G, Apel E D, Lemasters J J Protective effect of nitrendipine against hypoxic injury in perfused livers from ethanol-treated rats. *J Cardiovasc Pharmacol* 12 (Suppl 4), S113-6, 1988.

Vaidya A B, Antarkar D S, Doshi J C, Bhatt A D, Ramesh V, Vora P V, Perissond D, Baxi A J, Kale P M *Picrorhiza kurroa* (Kutaki) Royle ex Benth as a hepatoprotective agent—experimental & clinical studies. *J Postgrad Med* 42:105-8, 1996.

Vargas F, Cheng A T, Velutini G, Marcano E, Sanchez Y, Fraile G, Velasquez M. In vitro antioxidant and photooxidant properties of dipyridamole *Int J. Toxicol.* 20:363-8, 2001.

Wallace A E and Weeks W B. Thiamine treatment of chronic hepatitis B infection. Am J Gastroenterol 96: 864-8, 2001.

Wilson, J D. Vitamin deficiency and excess. (in) *Harrison's principles of Internal Medicine* published by McGraw-Hill, Health Professions Division, 1998.

The invention claimed is:

1. A method of treating a human subject suffering from viral hepatitis C without cirrhosis comprising the oral administration of a composition comprising a slow release formulation comprising diltiazem and thiamine to the subject, wherein diltiazem is administered in an amount of from 20 mg to 70 mg per day and the thiamine is administered in a dose of from 1 mg to 20 mg per day.

2. A method according to claim 1 wherein the slow release formulation provides a delivery rate sufficient to provide a clinical effective blood level of diltiazem in the portal vein and less than required to provide a clinically effective level of diltiazem in the peripheral circulation to thereby provide a delivery rate having a selective effect on the liver.

3. A method according to claim 1 wherein diltiazem is administered in an amount of less than 50 mg per day.

4. A method according to claim 1 wherein diltiazem is administered at a dose of from 20 to 50 mg per day and thiamine is administered at a dose of from 1 to 5 mg per day.

* * * * *